United States Patent
Taskin et al.

(10) Patent No.: US 10,391,217 B2
(45) Date of Patent: Aug. 27, 2019

(54) AXIAL FLOW IMPLANTABLE MECHANICAL CIRCULATORY SUPPORT DEVICES WITH OUTLET VOLUTE

(71) Applicant: HeartWare, Inc., Mounds View, MN (US)

(72) Inventors: Mustafa Ertan Taskin, Cooper City, FL (US); Charles R. Shambaugh, Jr., Coral Gables, FL (US)

(73) Assignee: HeartWare, Inc., Miami Lakes, FL (US)

(*) Notice: Subject to any disclaimer, the term of this patent is extended or adjusted under 35 U.S.C. 154(b) by 266 days.

(21) Appl. No.: 15/385,480

(22) Filed: Dec. 20, 2016

(65) Prior Publication Data

US 2017/0173240 A1 Jun. 22, 2017

Related U.S. Application Data

(60) Provisional application No. 62/270,189, filed on Dec. 21, 2015.

(51) Int. Cl.
*A61M 1/10* (2006.01)
*A61M 1/12* (2006.01)

(52) U.S. Cl.
CPC ............ *A61M 1/122* (2014.02); *A61M 1/101* (2013.01); *A61M 1/1012* (2014.02); *A61M 1/1031* (2014.02)

(58) Field of Classification Search
CPC .... A61M 1/122; A61M 1/101; A61M 1/1012; A61M 1/1031
See application file for complete search history.

(56) References Cited

U.S. PATENT DOCUMENTS

| 5,049,134 | A | 9/1991 | Golding et al. |
| 5,824,070 | A * | 10/1998 | Jarvik ................. A61M 1/1031 623/3.13 |
| 7,905,823 | B2 | 3/2011 | Farnan et al. |
| 7,972,122 | B2 | 7/2011 | LaRose et al. |
| 8,007,254 | B2 * | 8/2011 | LaRose ................. A61M 1/101 417/356 |
| 8,419,609 | B2 | 4/2013 | Shambaugh, Jr. et al. |

(Continued)

FOREIGN PATENT DOCUMENTS

| WO | 2007040663 A1 | 4/2007 |
| WO | 2011054545 A1 | 5/2011 |

OTHER PUBLICATIONS

International Search Report and Written Opinion dated Mar. 6, 2017, for corresponding International Application No. PCT/US2016/067841; International Filing Date: Dec. 20, 2016 consisting of 11-pages.

*Primary Examiner* — Rex R Holmes
(74) *Attorney, Agent, or Firm* — Christopher & Weisberg, P.A.

(57) ABSTRACT

A mechanical circulatory support device includes an inner housing having an inlet end, an outlet end, and a flow path there between. The flow path defines a longitudinal axis. A volute downstream of the outlet end has an outlet port. A rotor mounted within the inner housing upstream of the volute and configured to rotate about the longitudinal axis is included. The volute includes an inner surface having a minimum radius immediately adjacent the rotor and a maximum radius at the outlet port that is larger than the minimum radius.

20 Claims, 3 Drawing Sheets

(56) References Cited

U.S. PATENT DOCUMENTS

| | | |
|---|---|---|
| 8,768,487 B2 | 7/2014 | Farnan et al. |
| 2012/0095281 A1 | 4/2012 | Reichenbach et al. |
| 2014/0275723 A1 | 9/2014 | Fritz, IV et al. |
| 2015/0051438 A1 | 2/2015 | Taskin |

* cited by examiner

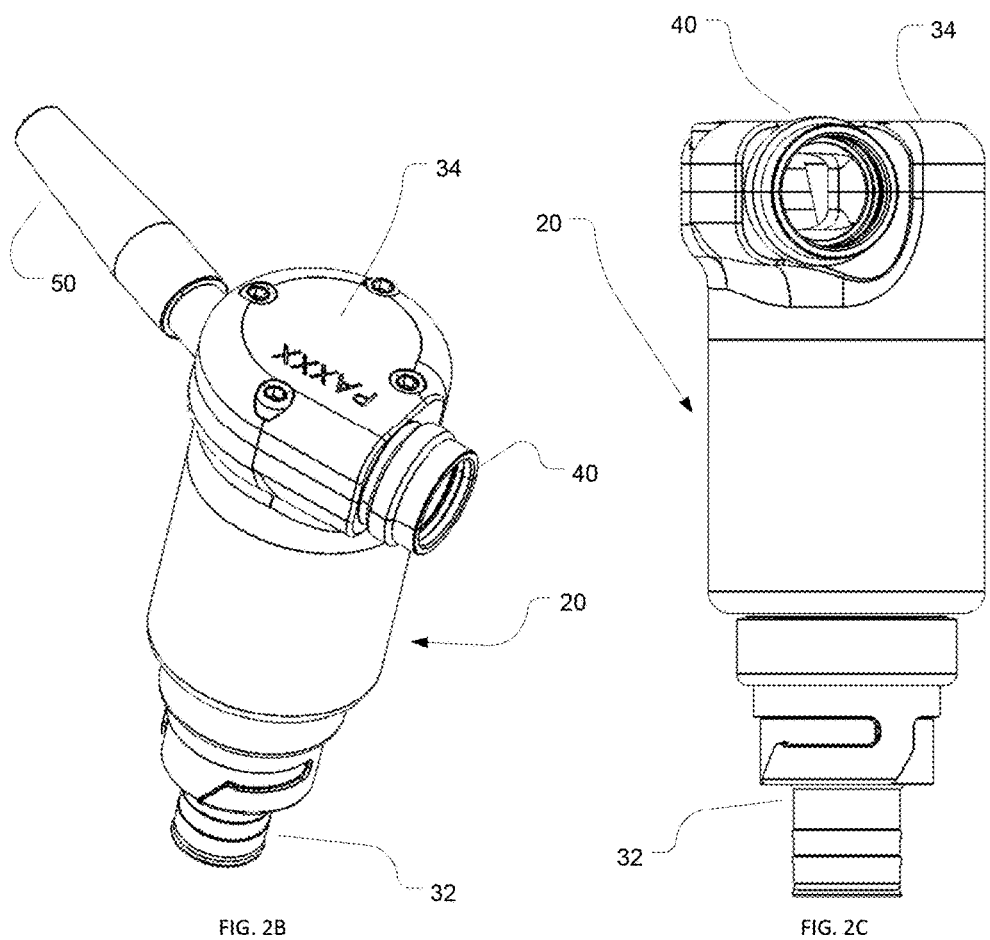

AXIAL FLOW IMPLANTABLE MECHANICAL CIRCULATORY SUPPORT DEVICES WITH OUTLET VOLUTE

CROSS-REFERENCE TO RELATED APPLICATION

This application is related to and claims priority to U.S. Provisional Patent Application Ser. No. 62/270,189, filed Dec. 21, 2015, entitled AXIAL FLOW IMPLANTABLE MECHANICAL CIRCULATORY SUPPORT DEVICES WITH OUTLET VOLUTE, the entirety of which is incorporated herein by reference.

STATEMENT REGARDING FEDERALLY SPONSORED RESEARCH OR DEVELOPMENT n/a

TECHNICAL FIELD

The present invention relates to mechanical circulatory support devices.

BACKGROUND

The present invention relates to mechanical circulatory support devices or "MCSDs." MCSDs are used to assist the pumping action of the heart. Certain MCSDs are used to assist the pumping action of a ventricle of the heart and, therefore, are referred to as "ventricular assist devices" or "VADs." For example, as shown in U.S. Pat. Nos. 7,972,122; 8,007,254; and 8,419,609, the disclosures of which are hereby incorporated by reference herein, one form of MCSD incorporates a generally cylindrical inner casing defining a flow path and a rotor mounted within the flow path for rotation about the axis of the flow path. The rotor is arranged to impel blood along the axis of the flow path. Electrical coils are mounted around the inner casing, and an outer casing surrounds the electrical coils. The coils provide a rotating magnetic field within the flow path. The rotor has a permanent magnetization that interacts with the rotating field so that the rotating field impels the rotor in rotation about the axis. The MCSD may include a volute that serves to redirect the flow from the axial direction to a direction transverse to the axis. The volute has an outlet connection that serves as the outlet connection of the MCSD.

Such a pump can be implanted within the thoracic cavity of a human patient as, for example, within the pericardial sack. The inlet end of the housing may be connected directly to the ventricle or connected to the ventricle by a short inlet cannula. The outlet connection may be connected, for example, to the aorta by an outlet cannula. Merely by way of example, a typical MCSD of this type has a capacity to pump about 7-10 liters per minute against a pressure difference or head of about 75 mm Hg, and thus can bear a substantial proportion or almost all of the pumping load typically carried by the left ventricle. Merely by way of example, the outer casing of such a pump may be about 21 mm in diameter, and the volute may have somewhat larger dimensions in a plane perpendicular to the axis.

Such intra-thoracic implantation requires invasive surgery, commonly requiring open-chest surgery which likely includes a sternotomy. Further, such positioning requires attaching the MCSD directly to the heart or within a chamber of the heart. While such procedures are high risk for any patient, they are particularly dangerous for patients in need of such MCSDs as they are typically in poor health and less likely to successfully undergo such surgeries.

Other MCSDs, such as those shown in U.S. Pat. Nos. 7,905,823 and 8,768,487 and in U.S. Patent Application Publication No. 2014/0275723, the disclosures of which are hereby also incorporated by reference herein, include generally similar elements but are of smaller size. These MCSDs typically implanted outside of the thoracic cavity as, for example, under the skin within the soft tissues of the pectoral area. These devices typically are connected to the heart as, for example, to the left atrium by an inlet cannula extending from the location of the pump to the atrium. The outlet of the pump typically is connected to an artery as, for example, the subclavian artery. Because the pump is implanted outside of the thoracic cavity, remote from the heart, the implantation procedure is considerably less invasive. Typically, the cannula can be inserted into a chamber of the heart by a laparoscopic or catheter-based procedure and threaded through the tissues of the body to the location of the pump. The procedure for inserting the outlet cannula is also performed outside of the thoracic cavity. Moreover, because the pump is located outside of the thoracic cavity, the pump can be accessed readily if it becomes necessary to repair or replace it.

MCSDs intended for extra-thoracic placement typically have been configured to provide lower pumping capacity than MCSDs intended for intra-thoracic implantation. For example, a typical MCSD intended for extra-thoracic implantation may provide a blood flow of about 1-4 liters per minute at a 75 mm Hg head. These MCSDs thus carry a smaller proportion of the pumping load of the heart. Such pumps typically have smaller dimensions than pumps intended for intra-thoracic implantation.

Extra-thoracically implanted MCSDs typically are housed in a pocket within the soft tissues outside of the thoracic cavity. Such pockets normally are created by surgical procedures as, for example, separating skin or subcutaneous fat from the underlying muscular tissue or separating layers of muscular tissue from one another. In some instances, the tissues forming the wall of a pocket surrounding an extra-thoracic MCSD can erode. Such erosion arises from mechanical action of the MCSD against the surrounding tissues. Mechanical action of the MCSD can lead to inflammation and necrosis of the tissues surrounding the pocket, and can cause the pocket to become enlarged. This difficulty can be particularly pronounced where the pocket closely overlies bones such as ribs. Enlargement of the pocket may allow movement of the MCSD, which creates an uncomfortable sensation for the patient. In severe cases, these conditions may require correction by additional surgical procedures.

Certain aspects of the present invention provide MCSDs and implantation methods that can address these concerns. Moreover, the improved MCSDs and implantation methods may allow implantation of larger MCSDs in extra-thoracic locations. For example, MCSDs of the type typically used heretofore for intra-thoracic implantation can be implanted extra-thoracically.

Currently available MCSDs that can accommodate intra-thoracic MCSD pumping capacity present drawbacks when used for extra-thoracic positioning due at least to the size and shape of the MCSD. For instance, the width of the volute of the aforementioned intrathoracic pump can pose difficulties in extra-thoracic implantation. As such, there is a need in the art for alternative MCSD designs that are suitable for intra-thoracic volumetric pumping capacity while being capable of extra-thoracic positioning within a patient.

SUMMARY

The present invention relates generally to an MCSD, the MCSD includes an inner housing having an inlet end, an outlet end, and a flow path there between. The flow path defines a longitudinal axis. A volute downstream of the outlet end has an outlet port. A rotor mounted within the inner housing upstream of the volute and configured to rotate about the longitudinal axis is included. The volute includes an inner surface having a minimum radius immediately adjacent the rotor and a maximum radius at the outlet port that is larger than the minimum radius.

In another aspect of this embodiment, an elongate housing portion disposed between the rotor and the volute is included, the elongate housing portion having an inlet end radius and an outlet end radius, the inlet end radius being at least one of larger than and equal to an inner surface radius of the inner housing, and the outlet end radius being larger than the inner surface radius of the inner housing.

In another aspect of this embodiment, a center post extending through at least a portion of the volute and through at least a portion of the elongate housing portion is included, the center post being downstream from the rotor.

In another aspect of this embodiment, the center post increases in diameter in a direction downstream from the elongate housing portion.

In another aspect of this embodiment, the center post is axially aligned with the fluid flow path.

In another aspect of this embodiment, the elongate housing portion defines a gap between the rotor and the center post.

In another aspect of this embodiment, the elongate housing portion includes a first part adjacent the rotor having an outward taper from the inlet end radius, and a second part downstream from the first part and being cylindrical.

In another aspect of this embodiment, the outlet port is substantially orthogonal to the longitudinal axis.

In another aspect of this embodiment, the rotor is configured to pump a fluid in the direction of the of the fluid flow path.

In another aspect of this embodiment, an outer casing coupled to the inner housing is included, and the device further includes a stator disposed between the inner housing and the outer casing.

In another aspect of this embodiment, the outlet port extends in a direction substantially orthogonal to the longitudinal axis.

In another embodiment, the MCSD includes an inner housing defining an inlet end, an outlet end, a flow path there between defining a first longitudinal axis. The flow path further defines a second longitudinal axis orthogonal to the first longitudinal axis and a third longitudinal axis orthogonal to both the second longitudinal axis and the first longitudinal axis. A rotor positioned within the inner housing along the flow path and configured to pump a fluid along the first longitudinal axis is included. A volute in fluid communication with the flow path and downstream of the outlet end is included, the volute having an outlet port extending a plane defined by the second longitudinal axis and the third longitudinal axis.

In another aspect of this embodiment, the outlet port is offset from the second longitudinal axis by approximately 20 degrees.

In another aspect of this embodiment, an elongate housing portion disposed between the volute and the rotor is included, the elongate housing portion having an inlet end radius and an outlet end radius, the inlet end radius being at least one of larger than and equal to an inner surface radius of the inner housing, and the outlet end radius being larger than the inner surface radius of the inner housing.

In another aspect of this embodiment, the elongate housing portion has a length of at least 2.5 mm.

In another aspect of this embodiment, a high stress volume within the elongate housing portion and the volute, at a 3 Liters/minute flow rate and a pressure of 90 mm Hg, is less than 29 $mm^3$.

In another aspect of this embodiment, an area wall shear stress within the elongate housing portion and the volute, at a 3 Liters/minute flow rate and a pressure of 90 mm Hg less than 38 $mm^2$.

In another aspect of this embodiment, a center post extending through at least a portion of the volute and through at least a portion of the elongate housing portions included, the center post being downstream from the rotor, and wherein the center post increases in diameter in a direction downstream from the elongate housing portion.

In another aspect of this embodiment, the center post is axially aligned with the fluid flow path, and wherein the elongate housing portion defines a gap between the rotor and the center post.

In yet another embodiment, the MCSD includes an inner housing having an inlet end, an outlet end, and a flow path there between, the flow path defining a longitudinal axis. A volute downstream of the outlet end having an outlet port orthogonal to the longitudinal axis is included. A rotor mounted within the inner housing upstream of the volute and configured to rotate about the longitudinal axis and to pump a fluid along the longitudinal axis. The volute includes an inner surface having a minimum radius immediately adjacent the rotor and a maximum radius at the outlet port that is larger than the minimum radius. An elongate housing portion is disposed between the volute and the rotor, the elongate housing portion having an inlet end radius and an outlet end radius, the inlet end radius being at least one of larger than and equal to an inner surface radius of the inner housing, and the outlet end radius being larger than the inner surface radius of the inner housing, the elongate housing portion includes a first part adjacent the rotor having an outward taper from the inlet end radius, and a second part downstream from the first part and being cylindrical. A center post extends through at least a portion of the volute and through at least a portion of the elongate housing portion, the center post is downstream from the rotor, and wherein the center post increases in diameter in a direction downstream from the elongate housing portion, the center post being axially aligned with the fluid flow path, and wherein the elongate housing portion defines a gap between the rotor and the center post.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 illustrates a cross-sectional view of one embodiment of an MCSD of the present invention;

FIG. 2A-2C are various views of the MCSD of FIG. 1;

DETAILED DESCRIPTION

Figures 1, 2A:
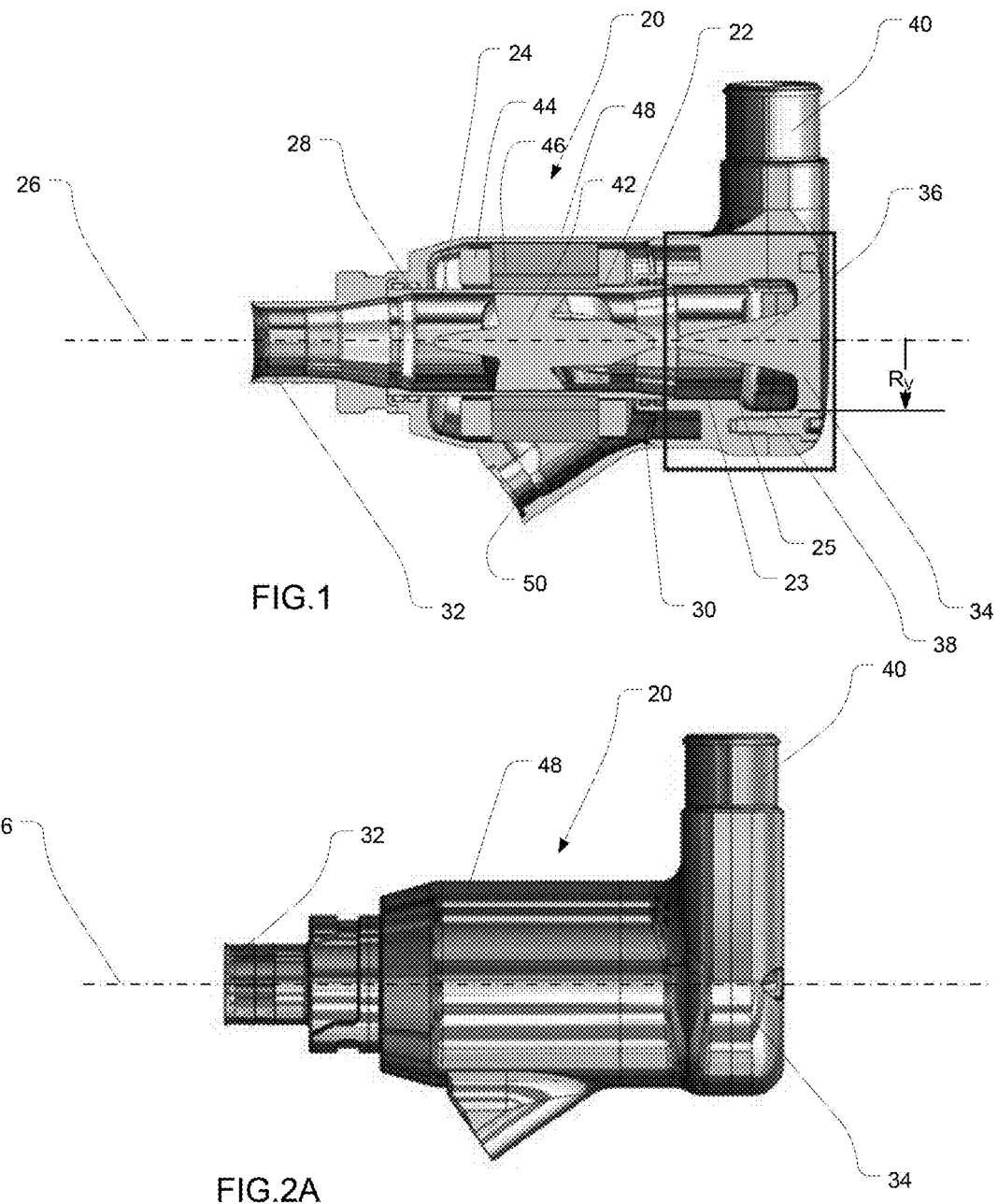

As used herein, relational terms, such as "first" and "second," "top" and "bottom," and the like, may be used solely to distinguish one entity or element from another entity or element without necessarily requiring or implying any physical or logical relationship or order between such entities or elements.

Now referring to the drawings in which like reference designators refer to like elements, there is shown in FIGS. 1-2A-2C a blood pump for mechanical circulatory support device according to one embodiment of the invention and designated generally as "20". The blood pump 20 may be generally as disclosed in the aforementioned U.S. Pat. Nos. 7,972,122; 8,007,254; and 8,419,609. The pump 20, illustrated as an axial flow pump for example, includes an inner housing 22 having an inner surface defining a generally cylindrical flow path 24 having an axis 26, an inlet end 28, and an outlet end 30. A hollow inlet fitting 32 projects axially from the inlet end 28 of the flow path and communicates with the flow path.

Following the flow path 24 through the outlet end 30 of the inner housing 22, the flow path transitions into an elongate housing portion 23. The elongate housing portion 23 projects axially from the outlet end 30 of inner housing 22 and communicates with the flow path 24. The elongate housing portion 23 has an inner surface defining the flow path 24 along axis 26 therethrough. The inner surface of the elongate housing portion 23 may be generally cylindrical, similar to the inner surface of the inner housing 22, or may have a widening taper along at least a portion or substantially all of the inner surface along a length of the flow path therethrough in the direction away from inner housing 22 (i.e., in the downstream direction). The elongate housing portion 23 has a radius at an inlet end, adjacent outlet 30 of inner housing 22, and a radius at an outlet end 25. The radius at the inlet end may be about the same radius as, or larger than, a radius of cylindrical flow path 24 and the radius at the outlet end 25 may be about the same as, or larger than, the radius at the inlet end of the elongate housing portion 23. The elongate housing portion 23 can have any length desired. For example, the length of portion 23 may be about 0.1 inches or greater. Further, the length of portion 23 can be, for example, 0.127 inches.

For ease of reference, the combined inner housing 22 and elongate housing portion 23 may generally be referred to as an inner casing which, while shown as a monolithic structure, can be separate connectable structures or the like, as desired. A volute 34 is connected to the outlet end 25 of the elongate housing portion 23 such that the flow path 24 through the elongate housing portion 23 transitions into the volute 34. The volute 34 includes a center post 36 extending generally in the axial direction through at least a portion of the elongate housing portion 23 and towards the inner housing 22. While the center post 36 extends along the axis 26 of the flow path 24, the center post 36 need not necessarily be centered within the flow path 24. The volute 34 defines a chamber 38 extending around the center post 36 and around axis 26. The volute 34 can also be monolithic with the inner casing (or just the elongate housing portion), or can be separate and attached to the inner casing using screws (as illustrated), welding, or the like.

As illustrated in FIG. 1, the flow path 24 through the elongate housing portion 23 is defined between its inner surface and an outer surface of an outer surface of center post 36. As illustrated in this embodiment, the flow path 24 through the elongate housing portion 23 narrows along its length from an inlet direction towards outlet end 25. Specifically, the outer surface of the center post 36 can include a widening taper, from an inlet direction towards an outlet direction, while the inner surface of the elongate housing portion includes either a widening taper (from an inlet direction towards outlet end 25), no taper (i.e., a cylindrical shape), or both (part of portion 23 is cylindrical and another part is tapered). For example, as illustrated in FIG. 1, the inner surface of the elongate housing portion 23 may include a widening taper at or adjacent to the inlet end of portion 23 and/or a widening taper at or adjacent to the outlet end 25, and remain generally cylindrical along the length between the inlet and outlet ends. To achieve a narrowing flow path, the widening taper of the center post 36 is larger than any widening taper of the elongate housing portion. In one configuration, if the elongate housing portion 23 is cylindrical, the widening taper of the center post 36 alone would also create such a narrowing flow path 24. For example, the widening taper of the center post 36 may extend at an angle of less than about 15 degrees relative to axis 26. In a further example, this angle may be between about 10 degrees and about 15 degrees. In yet another example, this angle may be about 12 degrees. Conversely, a line drawn extending from the inner surface at the inlet end of the elongate housing portion 23 to the inner surface at the outlet end 25, to establish an overall angle of the widening taper (if any) along the length of the elongate housing portion 23, may be less than about 10 degrees, for example. In another example, this mean angle may be less than about 5 degrees. In any event, this mean angle, establishing the angle of widening taper of the inner surface of the elongate housing portion 23, is less than the angle of widening taper of the center post 36.

Furthermore, the center post 36 can extend along at least a portion of the length of the elongate housing portion 23, or even through the entire elongate housing portion 23 up to or into a portion of the inner housing 22. As explained further below, to achieve the best flow characteristics through the pump 20, the center post 36 should be as long as possible. As such, as illustrated in the embodiment of FIG. 1, the center post 36 extends through substantially the entirety of the elongate housing portion 23 to an end point subjacent to, but not contacting, rotor 42 in inner housing 22. For example, there may be a gap of less than about 0.1 inches between the center post 36 and the rotor 42. This gap allows for a maximized length of the center post 36 while still providing a space to allow for small movements of the rotor 42 which may occur during normal operation, since contact between the rotor 42 and elements of the pump 20, including the center post 36, should be avoided. Alternative embodiments are also envisioned in which, for example, a shorter rotor 42 is used in the MCSD such that the center post 36 can extend further upstream and into a portion of the inner housing 22. Rotors of other shapes could also be used, and the upstream tip of the center post 36 could also be of a different shape so as to match the downstream end of such a rotor 42 to maintain beneficial fluid flow through the flow path 24.

Figure 3:
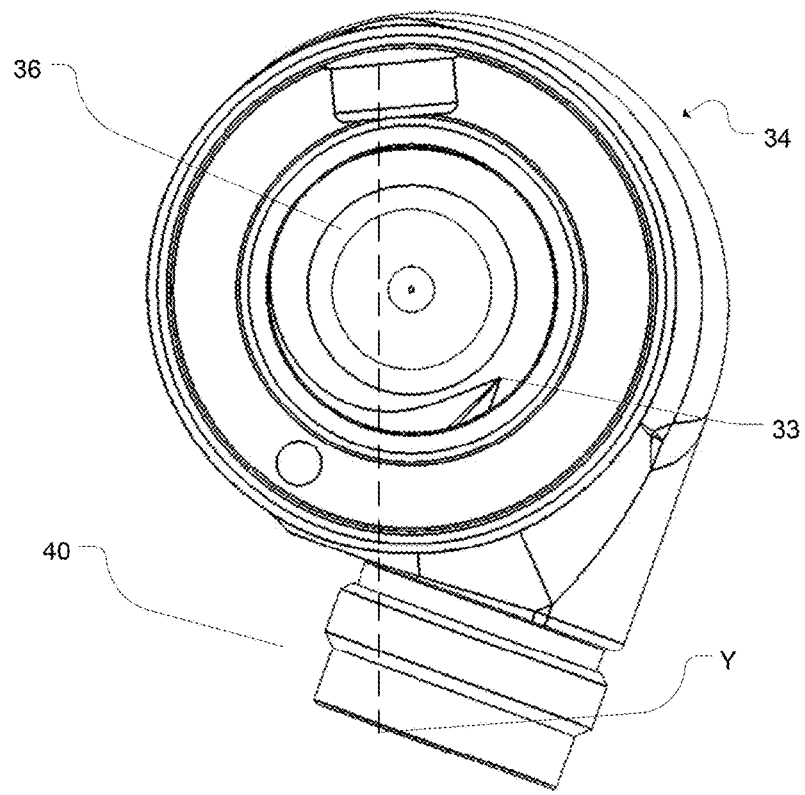
FIG. 3 is a cross-sectional view, viewed from the inlet end, of the volute structure of the embodiment of FIG. 1.
Figure 4:
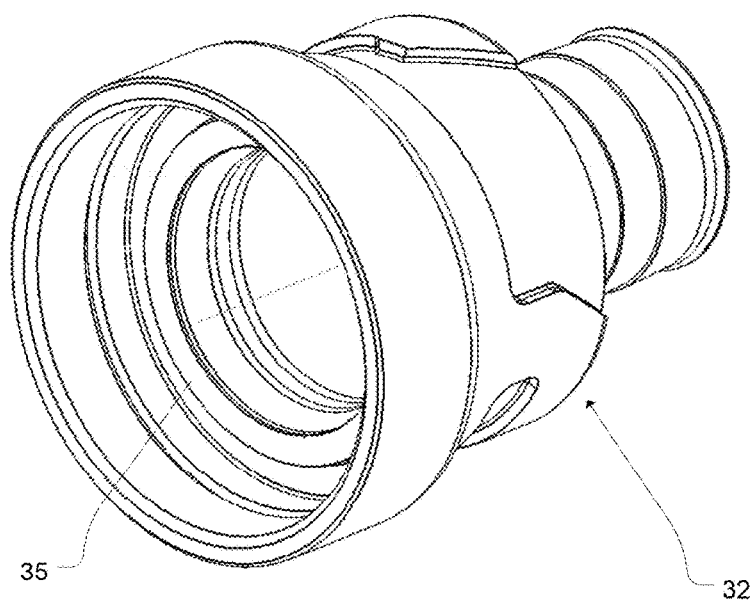
FIG. 4 is an isometric view of one embodiment of an inlet fitting of the present invention.

The chamber 38 of volute 34 has a radius $R_V$ measured from axis 26 to an inner surface of the chamber 38. The radius of the volute increases progressively in a circumferential direction around axis 26 from a minimum radius at a tongue 33 (FIG. 3) of the volute 34, adjacent to outlet end 25, increasing to a maximum radius towards an outlet port 40. As illustrated in FIGS. 1 and 3, the minimum radius may be about the same or larger than the radius at outlet end 25, as well as being greater than the radius of the cylindrical flow path 24 in the inner housing 22. Alternatively, the tongue 33 could be shaped such that the minimum radius is smaller than the radius at outlet end 25, the radius of the cylindrical flow path 24, and/or the radius of rotor 42. The flow path 24 through the volute chamber 38 is defined between the outer surface of center post 36 and the inner surface of the volute. The chamber 38 thus provides a widening flow path from the inlet of the volute (adjacent tongue 33 and outlet end 25 of the elongate housing portion) to the outlet port 40. The widening flow path 24 essentially may operate as a diffuser, in that the wider flow path results in a slowing speed of the fluid passing out of the pump 20 because of the increased volumetric capacity in the flow path 24. In one example, the progressive radius of the volute may range from a minimum radius of about 0.2273 inches to a maximum radius of about 0.3369 inches.

As best seen in FIGS. 2C and 3, the tubular outlet port 40 extends in a plane transverse to axis 26 and communicates with the volute chamber 38. In this way, the volute 34 converts angular momentum, imparted by the rotation of a rotor 42, into linear momentum in the direction of the outlet port 40. In this fashion, the fluid can then exit from the pump 20, through outlet port 40, in a linear fashion to enter the circulatory system of the patient, either human or animal. As illustrated, with the axis 26 (FIG. 1) considered to be the x-axis, the outlet port 40 extends in a yz plane, where the y-axis and z-axis both extend perpendicular to the x-axis and perpendicular to one another.

For example, in FIG. 3, a line Y designates the y-axis generally. The outlet port 40 is shown on the yz plane, but port 40 is offset from the y-axis. For instance, and as shown, this offset may be about 20 degrees. As discussed below, the positioning of the outlet port 40, relative to the rest of the pump body, depends upon the intended implantation location and orientation. However, this offset also may play a role in improved fluid flow through the MCSD. For instance, this offset effectively extends the pathway through the volute 34 past 360 degrees (relative to the tongue 33), such that the volute 34 can redirect the flow for a longer period of time. As such, the offset may act as if it were a larger volute (e.g., such as those in intra-thoracic MCSDs), which may improve fluid flow characteristics through the MCSD. In fact, the test data in Appendix A illustrates this factor as well.

A rotor 42 is disposed inside the flow path 24 defined by inner housing 22, such that the flow path 24 is defined along the inner surface of the inner housing and an outer surface of rotor 42. The rotor 42 desirably is symmetrical about an axis coincident with the central axis 26 of the flow path. In one configuration, the rotor 42 has a plurality of vanes spaced circumferentially around the axis and a plurality of channels between adjacent vanes. The vanes are configured to impel blood in the downstream direction along the axis upon rotation of the rotor about its axis in a predetermined direction. One particularly desirable rotor is disclosed in U.S. Patent Application Publication No. 2015/0051438 ("the '438 Publication"), the disclosure of which is also incorporated by reference herein. As also explained in the U.S. Pat. Nos. 7,972,122; 8,007,254; and 8,419,609 patents and in the '438 Publication, the rotor 42 is formed from a magnetic material such as a platinum-cobalt alloy and has a permanent magnetization in a direction transverse to the axis. The rotor 42 also has hydrodynamic bearing surfaces on the tips of the vanes, remote from axis 26. The pump 20 further includes electrical windings 44 carried on ferromagnetic metal cores 46. The windings 44 typically are composed of numerous turns of wire encircling the cores. Windings 44 are disposed in an array around the outside of inner casing 22. As best appreciated with reference to FIG. 5 in the copending, commonly assigned U.S. provisional patent application filed of even date herewith and entitled "IMPLANTABLE MECHANICAL CIRCULATORY SUPPORT DEVICES" (the "Co-Pending Application"), the disclosure of which is also incorporated by reference herein, the windings are disposed in pairs, with the windings of each pair being diametrically opposed to one another on opposite sides of the axis 26.

Commonly, the windings 44 may be energized in alternating sequence using a three-phase excitation system so as to create a rotating magnetic field within the flow path 24. Magnetic coupling between this rotating field and the permanent magnetization of rotor 42 drives the rotor 42 in rotation about the axis 26 of the flow path 24. As described in the aforementioned patents, the hydrodynamic bearing surfaces on the rotor 42 maintains the rotor 42 out of contact with the wall of inner housing 22 and with a thin film of blood disposed between the tip surface of each vane and the wall of the casing, and thus maintain the rotor with its axis aligned with the axis 26 of the flow path 24. Magnetic interaction between the magnetic field of the rotor and the ferromagnetic cores 46 of the stator prevents the rotor from moving axially. Rotation of the rotor 42 will tend to drive blood in a downstream direction, from the inlet end 26 of the flow path to the outlet end 30 of the inner housing 22, through the elongate housing portion 23 and out the outlet end 25 thereof, and out through the volute 34 and ultimately exiting through the outlet port 40.

An outer casing 48 surrounds the inner casing (inner housing 22 and elongate housing portion 23) and the windings and cores 44 and 46. Outer casing 48 may be generally cylindrical and coaxial with the inner casing and axis 26. The outer casing 48 is mechanically connected around the inner casing and forms a sealed enclosure around the windings. Electrical connections to the windings may be made through an opening 50 in the outer casing. This opening is sealed in an appropriate manner.

The inlet fitting 32, which projects axially from the inlet end 28 of the flow path 24 and communicates with the flow path 24, may be formed separately from the inner and outer casings and, as illustrated in FIGS. 1, 2A-2C and 4, is removably attachable to the inner and/or outer casings. For example, the inlet fitting 32 may include a screw thread connection to engage the inner casing. Other such removable attachments are also envisioned, such as separate screws, clasps, and the like. Alternatively, the inlet fitting may be monolithic, i.e. unitary, with another portion of the MCSD, such as the inner housing 22 or the inner casing, and/or with the outer housing 48. The inlet fitting can also include a reduced radius, adjacent inlet end 28, which effectively forms a mechanical stop 35 which can prevent the rotor 42 from exiting the housing through the inlet end. The reduced radius should be about the same as or less than the radius of the rotor 42.

The inlet fitting 32 is removable to allow for insertion and placement of the rotor 42 within the inner housing 22. Traditionally, the rotor 42 is inserted through the outlet end by removal of the volute 34, such that a removable inlet fitting was not necessary. However, in the present invention, the volute 42 can optionally be formed as a monolithic piece, during manufacture, with the inner casing (inner housing 22 and elongate housing portion 23) such that positioning the rotor 42 into the inner housing 22 via the outlet end would not be feasible. In any event, even if the volute is manufactured separately and welded, fixed by screws, or the like to the inner casing, the reduced diameter of the volute 34, and the extended length of the elongate housing portion 23 make it difficult and undesirable to place the rotor 42 via the outlet end. As such, the removable inlet fitting 32 provides for easier access to the inner housing 22 for placement of the rotor.

As mentioned above, the volute 34 of the present invention is of such a reduced size such that the pump 20 can be positioned in various locations of the anatomy of a patient, such as in between the ribcage and the skin. To minimize the dimensions of the pump as a whole transverse to axis 26, it is desirable to limit the maximum radius $R_V$ of the volute while still maintaining good flow characteristics such that the MCSD can fully support the pumping requirements of the patient. As representatively illustrated in FIG. 3, for example, the outlet port 40 is only partially radially offset from the flow path 24 and inner surface of the elongate housing portion 23 and volute 34. This configuration differs from traditional pump 20 configurations where the outlet port 40 would be more radially offset relative to the rest of the housing. As such, the outer radius of the volute is closer to the outer radius of the outer casing 48, both of which are relatively narrow as to typical intra-thoracic MCSDs. By way of example, the outer diameter of the outer casing 48 may be less than 1.0 inches, such as 0.822 inches. The outer diameter of the volute can also be less than 1.0 inches, such as about 0.90 inches. The elongate housing portion 23, and consequently the longer center post 36, allows the volute 34 to have a more compact size, such that the outlet port 40 is only partially radially offset relative to the flow path 24.

Such a smaller dimensioned volute 34, however, commonly leads to excess stress on the fluid, typically blood, which could cause damage to the blood, lead to clot formation within the MCSD, or result in undesirable wear on the components of the MCSD, in particular the rotor 42. Such fluid stress increases as blood flow increases. In one configuration, a high stress volume within the elongate housing portion and the volute, at a 3 Liters/minute flow rate and a pressure of 90 mm Hg, is less than 29 mm$^3$. The "high stress volume" is defined as the volume within the system where the shear stress exceeds a threshold. In one configuration, an area wall shear stress within the elongate housing portion and the volute, at a 3 Liters/minute flow rate and a pressure of 90 mm Hg is less than 38 mm$^2$. The area wall shear stress is defined as a maximum wall area of an inner surface of the inner casing exhibiting low shear stress.

In one embodiment, to reduce the stress within the system, the present invention of FIGS. 1 and 2A-2C includes the elongate housing portion 23 which provides additional length between the volute 34 and the rotor 42 to allow for an elongate center post 36. The added length of the center post 36 of this embodiment allows for a more gradual widening taper of the center post 36 to create a gradually narrowed flow path 24 to the volute 34. As such, the narrowing flow path 24 directs the fluid into the volute 34 where, due to the circular pathway through the volute, the fluid flow is redirected away from axis 26 to the outlet port 40. Thus, the elongate housing portion 23, extended center post 36 and reduced diameter volute of the present invention are capable of achieving the same volume, flow and stress characteristics of larger volutes and MCSDs, though the reduced size of the MCSD of the present invention allow for greater flexibility in placement of the MCSD in a patient's anatomy.

The inner casing, (i.e., the inner housing 22 and the elongate housing portion 23) and outer casing 48, and volute 34, may be shaped such that they can be positioned in a patient, for example, in between the ribcage and the skin of a patient. Further, the volute 34 and outflow port 40 are shaped to direct fluid from the pump to the circulatory system of the patient. For example, with the pump positioned in between the ribcage and the skin of a patient, the outlet port 40 can be positioned to direct the fluid flow through a conduit extending from the MCSD, in between two ribs of the ribcage (the intercostal space), and to the circulatory system, such as (in the case of left side heart support) the subclavian artery, the aorta, or the like. The outlet port may be offset from the y-axis, on the yz plane, as discussed above, by about 20 degrees to optimize such positioning relative to the ribcage. Furthermore, as discussed at length in the Co-Pending Application, a copy of which is annexed hereto, the MCSD may include a further housing 52 surrounding the outer casing 48 which may provide better positioning within the anatomy, such as between the ribcage and the skin.

In another embodiment, the present invention includes a method of assembling an MCSD. In this embodiment, the inner casing, including the inner housing 22 and elongate housing portion 23 is manufactured either monolithically formed or formed from two separate pieces and combined or connected during manufacture. Additionally, the volute 34 is either formed monolithically with the inner casing (or with the elongate housing portion 23 only) or is formed separately and attached with the inner casing, as desired. With the inner casing ready, the rotor is then directed through the inlet end of the inner casing and into the inner housing. As discussed throughout the various patent applications incorporated by reference herein, the magnetic attraction of the rotor to the metal cores 46, the rotor maintains its position within the inner housing. Finally, the inlet fitting is connected to the inner casing such that the inlet end of the inner casing contacts the inlet fitting. In this position, the mechanical stop 35 within the inlet fitting is positioned to prevent the rotor from exiting through the inlet end and out of the inner housing.

The aforementioned Co-Pending Application, incorporated by reference herein, discloses various MCSDs and implantation methods which may allow implantation of the MCSDs discussed above within the body of a human or non-human mammalian subject, at a location outside of the thoracic cavity of the subject. Further, such MCSDs and methods of implantation may allow larger MCSDs, such as the MCSDs discussed above, to be implanted in extra-thoracic locations. For example, MCSDs of the size and type typically used heretofore for intra-thoracic implantation can be implanted extra-thoracically. In one specific example, such an implantation procedure includes forming a pocket within the body of the subject at the location where the MCSD is to be implanted. Typically, the pocket is formed by forming a cut in tissues of the subject and separating adjacent layers of tissue. The MCSD is then inserted between the separated layers. More specifically, such a pocket can be formed between the ribcage and the skin of the subject, such that, for example, the MCSD can be positioned against the intercostal space between two ribs, and further, such that the outlet port 40 can be positioned through the intercostal space to communicate with the subject's vasculature via a conduit or the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A mechanical circulatory support device, comprising:
an inner housing having an inlet end, an outlet end, and a flow path there between, the flow path defining a longitudinal axis;
a volute downstream of the outlet end having an outlet port;
a rotor mounted within the inner housing upstream of the volute and configured to rotate about the longitudinal axis, the rotor having a proximal end and a distal end; and
the volute including an inner surface having a minimum radius immediately adjacent the distal end of the rotor and progressively increasing to a maximum radius at the outlet port.

2. The device of claim 1, further including elongate housing portion disposed between the rotor and the volute, the elongate housing portion having an inlet end radius and an outlet end radius, the inlet end radius being at least one of larger than and equal to an inner surface radius of the inner housing, and the outlet end radius being larger than the inner surface radius of the inner housing.

3. The device of claim 2, further including a center post extending through at least a portion of the volute and through at least a portion of the elongate housing portion, the center post being downstream from the rotor.

4. The device of claim 3, wherein the center post increases in diameter in a direction downstream from the elongate housing portion.

5. The device of claim 3, wherein the center post is axially aligned with the fluid flow path.

6. The device of claim 3, wherein the elongate housing portion defines a gap between the rotor and the center post.

7. The device of claim 2, wherein the elongate housing portion includes a first part adjacent the rotor having an outward taper from the inlet end radius, and a second part downstream from the first part and being cylindrical.

8. The device of claim 1, wherein the outlet port is substantially orthogonal to the longitudinal axis.

9. The device of claim 1, wherein the rotor is configured to pump a fluid in the direction of the of the fluid flow path.

10. The device of claim 1, further including an outer casing coupled to the inner housing, and wherein the device further includes a stator disposed between the inner housing and the outer casing.

11. The device of claim 1, wherein the outlet port extends in a direction substantially orthogonal to the longitudinal axis.

12. A mechanical circulatory support device, comprising:
an inner housing defining an inlet end, an outlet end, a flow path there between defining a first longitudinal axis,
the flow path further defining a second longitudinal axis orthogonal to the first longitudinal axis and a third longitudinal axis orthogonal to both the second longitudinal axis and the first longitudinal axis;
a rotor positioned within the inner housing along the flow path and configured to pump a fluid along the first longitudinal axis, the rotor having a proximal and a distal end;
a volute in fluid communication with the flow path and downstream of the outlet end, the volute progressively increasing in diameter from immediately distal of the distal end of the rotor toward an outlet port, the outlet port extending in a plane defined by the second longitudinal axis and the third longitudinal axis; and
an outer diameter of the mechanical circulatory device progressively increasing in diameter from the inlet end to the outlet port.

13. The device of claim 12, wherein the outlet port is offset from the second longitudinal axis by approximately 20 degrees.

14. The device of claim 12, further including an elongate housing portion disposed between the volute and the rotor, the elongate housing portion having an inlet end radius and an outlet end radius, the inlet end radius being at least one of larger than and equal to an inner surface radius of the inner housing, and the outlet end radius being larger than the inner surface radius of the inner housing.

15. The device of claim 14, wherein the elongate housing portion has a length of at least 2.5 mm.

16. The device of claim 14, wherein a high stress volume within the elongate housing portion and the volute, at a 3 Liters/minute flow rate and a pressure of 90 mm Hg, is less than 29 $mm^3$.

17. The device of claim 14, wherein an area wall shear stress within the elongate housing portion and the volute, at a 3 Liters/minute flow rate and a pressure of 90 mm Hg is less than 38 $mm^2$.

18. The device of claim 14, further including a center post extending through at least a portion of the volute and through at least a portion of the elongate housing portion, the center post being downstream from the rotor, and wherein the center post increases in diameter in a direction downstream from the elongate housing portion.

19. The device of claim 18, wherein the center post is axially aligned with the fluid flow path, and wherein the elongate housing portion defines a gap between the rotor and the center post.

20. A mechanical circulatory support device, comprising:
an inner housing having an inlet end, an outlet end, and a flow path there between, the flow path defining a longitudinal axis;
a volute downstream of the outlet end having an outlet port orthogonal to the longitudinal axis;
a rotor mounted within the inner housing upstream of the volute and configured to rotate about the longitudinal axis and to pump a fluid along the longitudinal axis, the rotor having a proximal end and a distal end;
the volute including an inner surface having a minimum radius immediately adjacent the rotor and a maximum radius at the outlet port that is larger than the minimum radius, the volute including an inner surface having a minimum radius immediately adjacent the distal end of the rotor and progressively increasing to a maximum radius at the outlet port;
an elongate housing portion disposed between the volute and the rotor, the elongate housing portion having an inlet end radius and an outlet end radius, the inlet end radius being at least one of larger than and equal to an inner surface radius of the inner housing, and the outlet end radius being larger than the inner surface radius of the inner housing, the elongate housing portion including a first part adjacent the rotor having an outward taper from the inlet end radius, and a second part downstream from the first part and being cylindrical, a maximum radius of the inner housing being less than a maximum radius of the elongate housing and the maximum radius of the elongate housing being less than the maximum radius of the volute; and a center post extending through at least a portion of the volute and through at least a portion of the elongate housing portion, the center post being downstream from the rotor, and wherein the center post increases in diameter in a direction downstream from the elongate housing portion, the center post being axially aligned with the fluid flow path, and wherein the elongate housing portion defines a gap between the rotor and the center post.

* * * * *